(12) United States Patent
Kang et al.

(10) Patent No.: US 8,021,408 B2
(45) Date of Patent: Sep. 20, 2011

(54) INSERTING DEVICE OF ARTIFICIAL BLOOD STENT

(75) Inventors: Sung-Gwon Kang, Yongin-si (KR); Sang-Yeop Song, Sungnam-si (KR)

(73) Assignee: S&G Biotech, Inc., Seoul (KR)

( * ) Notice: Subject to any disclaimer, the term of this patent is extended or adjusted under 35 U.S.C. 154(b) by 191 days.

(21) Appl. No.: 12/300,777

(22) PCT Filed: May 15, 2006

(86) PCT No.: PCT/KR2006/001808
§ 371 (c)(1),
(2), (4) Date: Nov. 13, 2008

(87) PCT Pub. No.: WO2007/132959
PCT Pub. Date: Nov. 22, 2007

(65) Prior Publication Data
US 2009/0248032 A1    Oct. 1, 2009

(51) Int. Cl.
*A61F 2/84* (2006.01)
(52) U.S. Cl. ...................... 623/1.11; 623/1.23

(58) Field of Classification Search .................. 606/108; 623/1.11, 1.12, 1.23
See application file for complete search history.

(56) References Cited

U.S. PATENT DOCUMENTS

| | | | |
|---|---|---|---|
| 6,302,891 B1 * | 10/2001 | Nadal | 606/108 |
| 6,878,158 B2 | 4/2005 | Shin et al. | |
| 2002/0151953 A1 * | 10/2002 | Chobotov et al. | 623/1.11 |
| 2006/0036263 A1 | 2/2006 | Stinson | |

FOREIGN PATENT DOCUMENTS

KR   20-0312490 Y1   5/2003

* cited by examiner

*Primary Examiner* — Ryan J Severson
(74) *Attorney, Agent, or Firm* — Birch, Stewart, Kolasch & Birch LLP

(57) ABSTRACT

An artificial blood stent insertion device which includes a blood stent having a front end portion, a middle portion and a rear end portion compressed by a fixing wire having ring-shaped loops disposed at the sides thereof, and a core passing through the loops and extending through the moving tube so that one end thereof is accessible, whereby the artificial blood stent can be easily inserted and fixed to a desired position in a blood vessel without affecting blood pressure, and then the artificial blood stent is expanded by disengaging the core from the loops of the fixing wire.

2 Claims, 2 Drawing Sheets

US 8,021,408 B2

INSERTING DEVICE OF ARTIFICIAL BLOOD STENT

TECHNICAL FIELD

The present invention relates to a device for inserting an artificial blood stent that is to be inserted into a lesion, such as a blood vessel aneurysm, for protecting the blood vessel, and more particularly, to an artificial blood stent insertion device of which provides easy workability in the insertion and placement into a lesion in a blood vessel by minimizing the effect of resistance caused by the flow of blood pressure in the procedure of inserting and placing an artificial blood stent into a blood vessel.

Generally, an aneurysm occurs in a blood vessel when part of the blood vessel swells like a balloon due to aging or other diseases.

The swollen part of the aneurysm has the risk of rupture due to a blood pressure.

In case of occurring such an aneurysm in a blood vessel, artificial blood replacement or bypass construction has been used in the swollen part mainly through a surgical operation. However, this method is disadvantageous in that the lesion needs to be cut open, which leaves a big scar, and the operational effect is not that satisfactory.

BACKGROUND ART

Due to the above problems, in recent years, there have been disclosed various methods of treatment without an operation. One of them is an artificial blood stent using a superelastic shape memory alloy wire.

As shown in FIG. 1, such an artificial blood stent 1 has such a shape that a hollow cylindrical connector, prepared to have a plurality of spaces and a predetermined length by weaving superelastic shape memory alloy wires, is attached to both sides of a main body made of fabric.

In addition to the artificial blood stent 1 illustrated in FIG. 1, various types of artificial blood stents 1 are recently utilized.

Such an artificial blood stent 1 is inserted into a lesion in a blood vessel by a separate insertion device, with its volume contracted to the minimum, and thereafter blocks an aneurysm region (swollen part) as it returns to its expanded shape, thereby preventing the risk of rupture due to a blood pressure.

Typically, an artificial blood stent insertion device comprises a moving tube 3 with a grip 8 fixed to one end inserted and placed into an outer tube 2 in front of a connector 7 so as to be movable back and forth, a guide passing tube 4 inserted and placed into the moving tube 3 for guiding a guide wire, and a cylindrical artificial blood stent 1 with a minimized diameter inserted between the moving tube 3 and the outer tube 2 and then placed into a blood vessel by pushing the moving tube 3 into the outer tube 2.

However, in case of using the aforementioned conventional device, the artificial blood stent 1 reassumes its expanded shape in the blood vessel by its elasticity the instant it is released from the insertion device. Due to this, in case of a high blood pressure, the artificial blood stent 1 is pushed down the blood vessel by the resistance caused by the flow of blood, thus it becomes difficult to accurately place the artificial blood stent 1 at a desired position in a blood vessel.

Due to these problems, a patent has to take antihypertensive agents in order to lower the blood pressure of the patient prior to an operation, and consequently the treatment costs increase and the risk of medical accidents become higher.

To overcome the above-described conventional problems, Korean Patent Laid-Open No. 2001-18324 proposes an artificial blood stent insertion device, which, in a case where the placement position of the artificial blood stent is wrongly selected due to the rear end of the stent woven into a wire, is capable of resetting a placement position after returning the artificial blood stent to its original position in the inside of the outer tube by pulling the stent along with an insertion tube.

However, the above insertion device still has the problem that the front end portion of the artificial blood stent being pushed out of the insertion device is immediately extended and grown when placing the artificial blood stent 1 in a blood vessel, and thus the artificial blood stent 1 is pushed down the blood vessel by being pushed by the flow of blood in the blood vessel.

To overcome the above-mentioned problem, Korean Utility Model Registration No. 20-0312490 proposes an artificial blood stent insertion device, as shown in FIG. 5, in which a wire hole 4'c is formed on the front end portion of a connecting tube 4' to insert one end of a fixing wire 6 therein in a loop 6b shape, a core 5 projected to extend from the inside of the connecting tube 4' to the outside of a grip 8 is inserted into the loop 6b of the fixing wire 6 for supporting it, and the other end of the fixing wire 6 is tied in a manner to surround only the front end portion of stent 1.

FIG. 5 is a cross sectional view showing the front end portion of the artificial blood stent 1 fixed by the core 5 by being tied into a contracted state by the fixing wire 6 in the artificial blood stent insertion device disclosed in the above Utility Model Registration No. 20-0312490.

However, the insertion device is disadvantageous in that the preparation for an operation is complex because it is necessary to make a knot 6c by tying the front end portion of the artificial blood stent 1 with the fixing wire 6, and when the stent is released from the outer tube, though the front end portion of the stent 1 is not immediately expanded, the middle portion and rear end portion of the stent 1 are immediately expanded and grown by its elasticity.

Due to this, the phenomenon that the stent 1 is pushed down the blood vessel by the resistance caused by the flow of blood in the blood vessel still occurs, thereby making it difficult to place the stent 1 at a desired position in a blood vessel.

Additionally, the above-described insertion device has a problem that the middle portion and rear end portion of the stent released from the outer tube is immediately expanded and grown and comes into contact with the walls of adjacent blood vessels even before removing the core 5, which makes it very difficult to find a desired vascular position and place and fix the artificial blood stent after extracting the artificial blood stent from the outer tube.

DISCLOSURE OF THE INVENTION

Accordingly, it is an object of the present invention to provide an artificial blood stent insertion device which can simultaneously overcome the problems described above.

The present invention provides an artificial blood stent insertion device which can easily insert and fix an artificial blood stent 1 at a desired position in a blood vessel without being affected by blood pressure. Furthermore, the present invention provides an artificial blood stent insertion device which can simplify the preparation for an operation since no knitting is required when tying an artificial blood stent 1 by a fixing wire 6.

Furthermore, the present invention provides an artificial blood stent insertion device which can easily adjust the placement position of the artificial blood stent insertion device even after pushing the artificial blood stent 1 out of an outer tube 2 by keeping the entire contracted state of the artificial blood stent 1 released out of the outer tube 2 until the removal of the core 5 by the artificial blood stent 1.

To achieve the above object, there is provided an artificial blood stent insertion device for use in vessel surgery according to the present invention, comprising: a moving tube 3 with a grip 8 fixed to one end inserted and placed into an outer tube 2 in front of a connector 7 so as to be movable back and forth, a guide passing tube 4 inserted and placed into the moving tube 3 for guiding a guide wire, and a cylindrical artificial blood stent 1 with a minimized diameter inserted between the moving tube 3 and the outer tube 2, and then inserted and placed into a blood vessel by pushing the moving tube 3 into the outer tube 2, wherein the front end portion, middle portion and rear end portion of the artificial blood stent 1 inserted into the outer tube 2 are tied, respectively, in such a manner to be surrounded by a fixing wire 6 having ring-shaped loops 6a at both sides, the fixing wire 6 is fixed by a core 5 passing through the loops 6a, and the core 5 passes through the moving tube so that one end thereof is projected to one side of the grip 8.

BRIEF DESCRIPTION OF THE DRAWINGS

These and other features, aspects, and advantages of preferred embodiments of the present invention will be more fully described in the following detailed description, when taken in conjunction with accompanying drawings. In the drawings.

BEST MODES FOR CARRYING OUT THE INVENTION

Hereinafter, the present invention will be described in detail with reference to the accompanying drawings.

Figure 1:
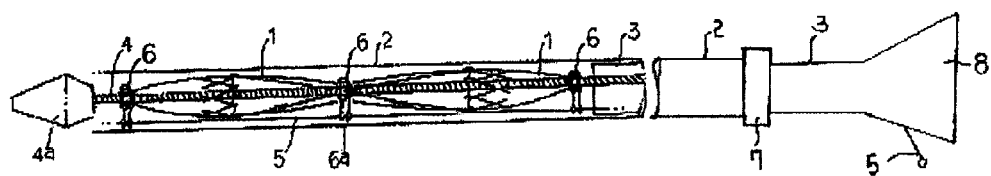
FIG. 1 is a cross sectional schematic diagram of the present invention.

First, as shown in FIG. 1, an artificial blood stent insertion device according to the present invention comprises a moving tube 3 with a grip 8 fixed to one end inserted and placed into an outer tube 2 in front of a connector 7 so as to be movable back and forth, a guide passing tube 4 inserted and placed into the moving tube 3 for guiding a guide wire, and a cylindrical artificial blood stent 1 with a minimized diameter inserted between the moving tube 3 and the outer tube 2, and then placed into a blood vessel by pushing the moving tube 3 into the outer tube 2.

FIG. 1 is a cross sectional schematic diagram of the present invention.

Figure 2:
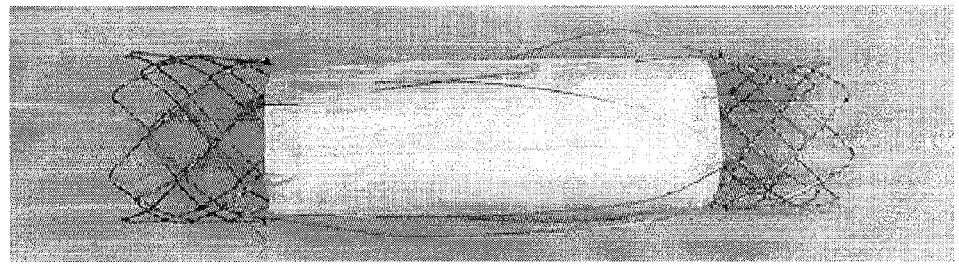
FIG. 2 is a photograph of one example of an artificial blood stent 1 used in the present invention.

As shown in FIG. 2, the artificial blood stent 1 to be used in the present invention has a structure in which connectors having shape memory alloy wires woven in a cylindrical shape so as to form spaces are attached to both ends of a stent main body made of fabric.

In the present invention, the shape of the artificial blood stent 1 is not specifically restricted.

FIG. 2 is a photograph of one example of an artificial blood stent 1 used in the present invention.

Figure 3:
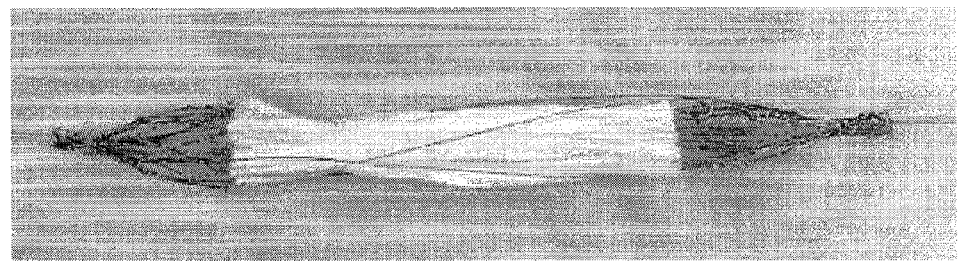
FIG. 3 is a photograph of three points of the artificial blood stent 1 of FIG. 2 being tied by a fixing wire 6.
Figure 4:
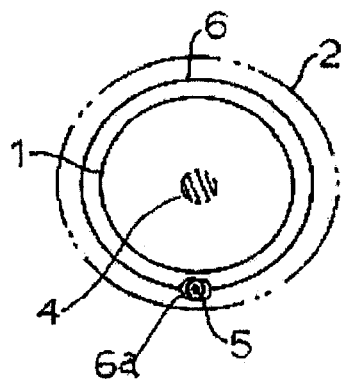
FIG. 4 is a cross sectional view showing the artificial blood stent 1 fixed by a core 5 by being tied into a contracted state by a fixing wire 6 according to the present invention.
Figure 5:
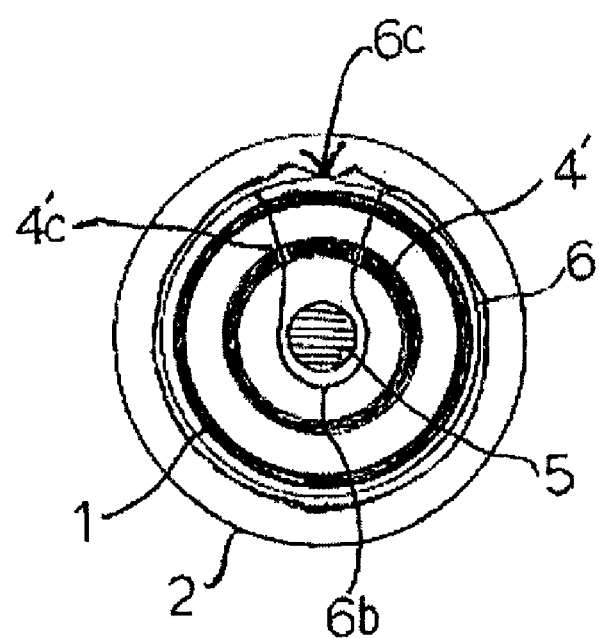
FIG. 5 is a cross sectional view showing the front end portion of an artificial blood stent 1 fixed by a core 5 by being tied into a contracted state by a fixing wire 6 in a conventional artificial blood stent insertion device.

In the present invention, as shown in FIGS. 3 and 4, the front end portion, middle portion and rear end portion of the artificial blood stent 1 inserted into the outer tube 2 are tied, respectively, in such a manner to be surrounded by a fixing wire 6 having ring-shaped loops 6a at both sides, the fixing wire 6 is fixed by a core 5 passing through the loops 6a, and the core 5 passes through the moving tube so that one end thereof is projected to one side of the grip 8.

FIG. 3 is a photograph of three points of the artificial blood stent 1 of FIG. 2 being tied by the fixing wire 6. FIG. 4 is a cross sectional view showing the artificial blood stent 1 fixed by the core 5 by being tied into a contracted state by the fixing wire 6.

It is preferable that the front end portion and rear end portion of the artificial blood stent 1 are firmly tied by the fixing wire 6 as compared to the middle portion thereof.

An insertion piece 4a is formed on the front end of the guide passing tube 4.

In the present invention, the middle portion and rear end portion of the artificial blood stent 1, as well as the front end portion thereof, are fixed by the core 5 by being tied into a contracted state by the fixing wire 6. Hence, when they are released from the outer tube 2 and placed in a blood vessel, the resistance caused by the flow of blood becomes less, thus preventing the artificial blood stent 1 from being pushed down the blood vessel and making it easier to place the artificial blood stent 1 at a desired position in the blood vessel.

Additionally, in the present invention, even in a case where the artificial blood stent 1 is released from the outer tube 2 and positioned in the blood vessel, the artificial blood stent 1 is kept tied in a contracted state over the entire longitudinal direction until the removal of the core 5, which enables it to place the artificial blood stent 1 after moving it until it reaches a desired position in the blood vessel.

Moreover, in the present invention, the fixing wire 6 having tied the artificial blood stent 1 is fixed in a manner that the core 5 passes through the loops 6a formed at both ends of the fixing wire 6, thus it is unnecessary to knit the fixing wire 6.

Next, a method of use of the present invention will be described.

First, an artificial blood stent 1 of a proper size is selected according to the length of a lesion, such as vascular aneurysms.

Next, the artificial blood stent 1 is inserted into a guide passing tube 4, then the front end portion, middle portion and rear end portion of the artificial blood stent 1 are tied by a fixing wire 6 to contract the diameter thereof, and then a core 5 passing through a moving tube 3 so that one end thereof is projected to one side of a grip 8 is inserted and fixed into loops 6a of the fixing wire.

Next, the moving tube 3 is pulled out from the inside of the outer tube 2 so that the artificial blood stent 1 in a contracted state is inserted and positioned into the outer tube 2. Once the insertion work of the artificial blood stent 1 into the insertion device is finished, the outer tube 2 is inserted and positioned until it reaches the front of a lesion in a blood vessel by an angioplasty technique.

In this state, with the grip 8 being held, the outer tube 2 is pulled along with a connector 7, that is, the moving tube 3 is pushed into the outer tube 2, such that the artificial blood stent 1 inserted into the outer tube 2 is released out of the outer tube 2 and positioned in the blood vessel.

At this time, the front end portion, middle portion and rear end portion of the artificial blood stent 1 being pushed out of the outer tube 2 are tied in such a manner that the fixing wire 6 surrounds the outer circumferential surface thereof. The fixing wire 6 is supported by the core 5, thus the artificial blood stent 1 is kept contracted without being expanded until the removal of the core 5 even if the artificial blood stent 1 is released out of the outer tube 2.

Next, the artificial blood stent 1 released from the outer tube 2 is moved to a desired position in the blood vessel, and then the core 5 is pulled so that the core 5 is released out from the loops 6a of the fixing wire, thereby loosening the fixing wire 6 tying the artificial blood stent 1.

Once the fixing wire 6 is loosened, the front end portion, middle portion and rear end portion of the artificial blood stent 1 are expanded to their original shape and closely placed on the lesion in the blood vessel.

The present invention is advantageous in that a patient does not need to take antihypertensive agents before an operation because the artificial blood stent 1 can be easily inserted and fixed to a desired position in a blood vessel without being affected by blood pressure. Additionally, the present invention is advantageous in that no knitting is required when tying the artificial blood stent 1 by the fixing wire 6, thereby simplifying the preparation for an operation.

Additionally, the present invention is advantageous in that the artificial blood stent 1 is kept contracted over the entire length until the removal of the core 5 even if the artificial blood stent 1 is released out of the outer tube 2, which makes it easier to adjust the placement position of the artificial blood stent 1 in the blood vessel.

INDUSTRIAL APPLICABILITY

The present invention is used for an operation for treatment of a lesion, such as aneurysms, by insertion.

The invention claimed is:

1. An artificial blood stent insertion device for use in vessel surgery which comprises:
   a moving tube and an outer tube, said moving tube being slidably disposed to move back and forth within the outer tube, said moving tube being provided with a grip member positioned at one end thereof,
   a guide passing tube slidably and axially disposed within the outer tube, and
   a cylindrical, artificial blood stent disposed between the moving tube and the outer tube, said blood stent being operatively compressed by a fixing wire to the guide passing tube at a front end portion, a middle portion and a rear end portion of said blood stent such that the compression at the front end and rear end portions is greater than the compression at the middle portion, said fixing wire being provided with loops disposed at the sides thereof, and
   a core member passing through the loops of the fixing wires and through the moving tube and terminating at the grip member,
   wherein the artificial blood stent is positioned within a blood vessel by pushing the moving tube into the outer tube, displacing the artificial blood stent from the outer tube and disengaging the core member from the loops of the fixing wires causing the artificial blood stent to expand to its cylindrical shape.

2. The artificial blood stent insertion device for use in vessel surgery of claim 1, wherein an insertion piece comprising a blunt end portion is formed on the front end of the guide passing tube.

\* \* \* \* \*